(12) United States Patent
DesOrmeaux et al.

(10) Patent No.: US 9,945,030 B2
(45) Date of Patent: Apr. 17, 2018

(54) FREE-STANDING SILICON OXIDE MEMBRANES AND METHODS OF MAKING AND USING SAME

(71) Applicant: SiMPore, Inc., West Henrietta, NY (US)

(72) Inventors: Jon-Paul DesOrmeaux, Rochester, NY (US); Christopher C. Striemer, Rochester, NY (US)

(73) Assignee: SiMPore Inc., West Henrietta, NY (US)

( * ) Notice: Subject to any disclaimer, the term of this patent is extended or adjusted under 35 U.S.C. 154(b) by 0 days.

(21) Appl. No.: 15/037,542

(22) PCT Filed: Nov. 19, 2014

(86) PCT No.: PCT/US2014/066383
§ 371 (c)(1),
(2) Date: May 18, 2016

(87) PCT Pub. No.: WO2015/077324
PCT Pub. Date: May 28, 2015

(65) Prior Publication Data
US 2016/0340778 A1 Nov. 24, 2016

Related U.S. Application Data

(60) Provisional application No. 61/906,109, filed on Nov. 19, 2013.

(51) Int. Cl.
*C23C 16/40* (2006.01)
*G02B 21/34* (2006.01)
*G01N 21/03* (2006.01)
*H01J 37/20* (2006.01)
*C23C 16/505* (2006.01)
*C23C 16/56* (2006.01)
*C23C 16/01* (2006.01)

(52) U.S. Cl.
CPC ............ *C23C 16/402* (2013.01); *C23C 16/01* (2013.01); *C23C 16/401* (2013.01); *C23C 16/505* (2013.01); *C23C 16/56* (2013.01); *G01N 21/03* (2013.01); *G02B 21/34* (2013.01); *H01J 37/20* (2013.01)

(58) Field of Classification Search
CPC .... B01D 67/00; B01D 67/0062; B01D 71/02; C23C 16/402; C23C 16/401; C23C 16/56; G01N 21/03; G02B 21/34; H01J 37/20
See application file for complete search history.

(56) References Cited

U.S. PATENT DOCUMENTS 5,753,014 A 5/1998 Van Rijn
2005/0051841 A1 3/2005 Leedy
(Continued)

FOREIGN PATENT DOCUMENTS

JP H18115912 5/1996

*Primary Examiner* — Nicole Ippolito
(74) *Attorney, Agent, or Firm* — Hodgson Russ LLP

(57) ABSTRACT

Provided is a free-standing silicon oxide film that is under tensile stress. Also, provided are methods of making a free-standing silicon oxide film that is under tensile stress. The methods use low-power PECVD deposition of silicon oxide. Methods of imaging one or more objects (e.g., cells) using a free-standing silicon oxide film that is under tensile stress is also provided.

13 Claims, 11 Drawing Sheets

(56) References Cited

U.S. PATENT DOCUMENTS

| | | |
|---|---|---|
| 2005/0176174 A1* | 8/2005 | Leedy ................ G03F 7/70658 438/107 |
| 2006/0273065 A1 | 12/2006 | Kim et al. |
| 2010/0032812 A1 | 2/2010 | Sedkey et al. |
| 2010/0062224 A1* | 3/2010 | Witvrouw ........... B81C 1/00246 428/172 |
| 2012/0077289 A1 | 3/2012 | Henley |
| 2013/0012087 A1 | 1/2013 | Itoh et al. |

* cited by examiner

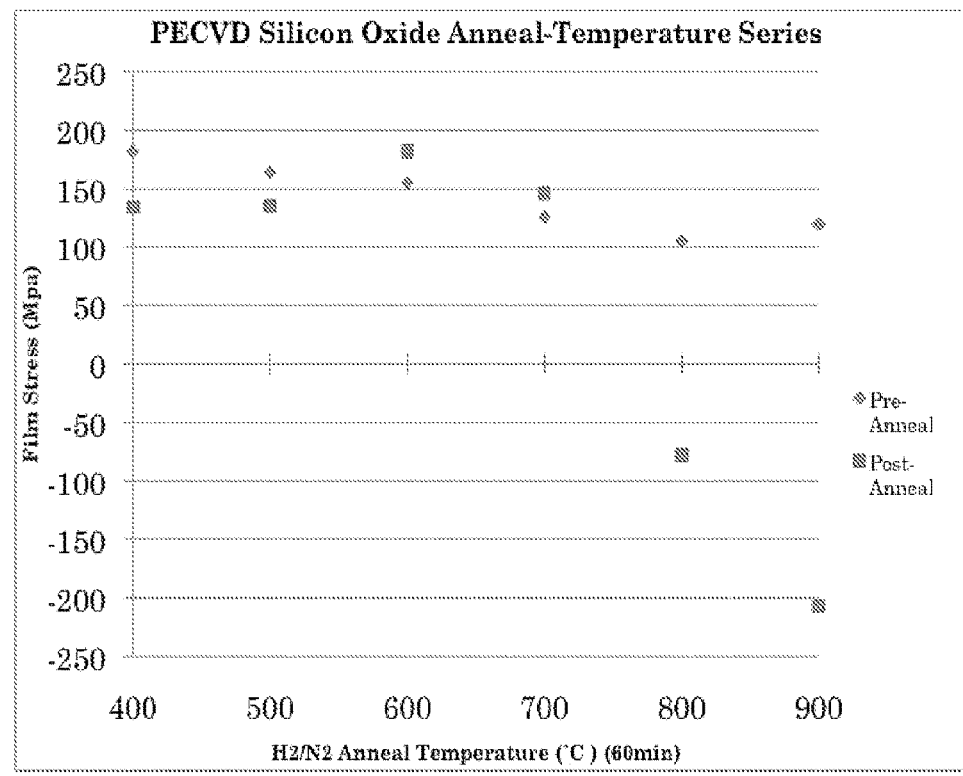
FIGURE 5
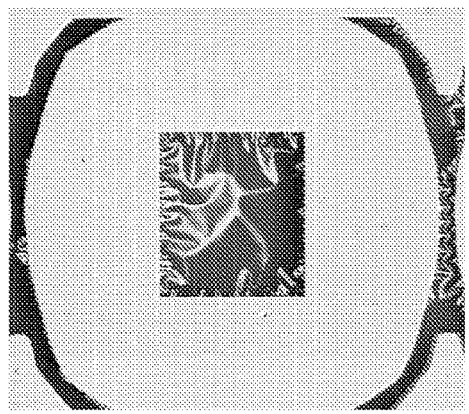 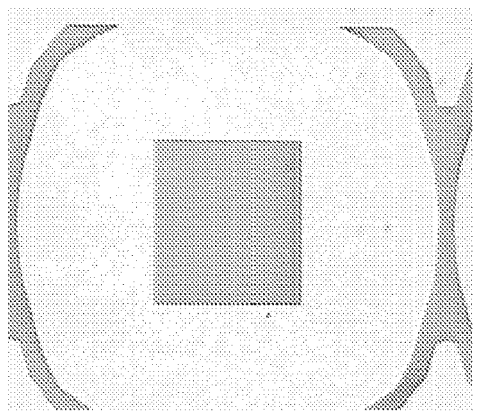
FIGURE 6A  FIGURE 6B

FREE-STANDING SILICON OXIDE MEMBRANES AND METHODS OF MAKING AND USING SAME

CROSS-REFERENCE TO RELATED APPLICATIONS

This application claims priority to provisional patent application No. 61/906,109 filed Nov. 19, 2013, the disclosure of which is hereby incorporated by reference.

BACKGROUND OF THE DISCLOSURE

Silicon dioxide is a low index, highly transparent, and biologically inert material that is a desirable substrate for imaging. However, silicon dioxide is typically under compressive strain as a deposited thin film. When such films are underetched to form free-standing membranes, they wrinkle. Wrinkling creates a nonplanar surface which results in extremely small focal planes (non-ideal for imaging).

BRIEF SUMMARY OF THE DISCLOSURE

In an aspect, the present disclosure provides a free-standing silicon oxide film that is under tensile stress. In an embodiment, the silicon oxide film is substantially flat. In an embodiment, the silicon oxide film is microporous. In an embodiment, the film has a thickness of 5 nm to 5000 nm. In an embodiment, the film has an area of 0.0625 mm$^2$ to 400 mm$^2$.

In an aspect, the present disclosure provides a method of forming a free-standing silicon oxide film comprising: a) depositing a silicon oxide film using plasma-enhanced chemical vapor deposition (PECVD) on a substrate configured to release at least a portion of the silicon oxide film as a free-standing film, where the PECVD is configured to deposit said silicon oxide film under tensile stress; b) annealing the silicon oxide film using a thermal process; and c) exposing at least a portion of the silicon oxide film such that a free-standing silicon oxide film is formed. In an embodiment, the PECVD occurs at an RF power between 80 W and 120 W. In an embodiment, the thermal process is carried out at a temperature between 550° C. and 700° C. In an embodiment, the thermal process occurs in an atmosphere comprising hydrogen or hydrogen and nitrogen. In an embodiment, the thermal process has a duration of between approximately 0.01 hour and approximately 24 hours. In an embodiment, the silicon oxide film is substantially flat after the annealing step.

In an embodiment, a method of obtaining an image comprises: a) providing a sample comprising one or more objects to be imaged disposed on a free-standing silicon oxide membrane of the present disclosure; and b) obtaining an image of at least one object or at least a portion of one object. In an embodiment, the one or more objects are cells, sub-cellular constituents, viruses, particles, powders, thin-films, or a combination thereof. In an embodiment, the image is obtained by optical microscopy, fluorescence microscopy, confocal microscopy, two-photon microscopy, or electron microscopy.

BRIEF DESCRIPTION OF THE FIGURES

FIG. 5. A Plot of anneal temperature vs. PECVD silicon oxide tensile stress (post deposition).

FIG. 6A-FIG. 6D. Optical images of free-standing PECVD silicon oxide membranes following low-power deposition (100 W) (FIG. 6A and FIG. 6C) and after H$_2$/N$_2$ gas annealing (600° C.) (FIG. 6B and FIG. 6D). FIG. 6A and FIG. 6B are 100 nm-thick PECVD silicon oxide films, freestanding over a 0.50 mm×0.50 mm area. FIG. 6C and FIG. 6D are 40 nm-thick PECVD silicon oxide films, freestanding over a 0.05 mm×0.05 mm area.

FIG. 7A—a PECVD silicon oxide after an 1 hour anneal in H$_2$/N$_2$ will remain tensile for at least 700 hours but become less tensile over that period. FIG. 7B—a PECVD silicon oxide after an 8 hour anneal in H$_2$/N$_2$ will remain tensile for at least 700 hours and with no appreciable decrease in tensile stress (i.e., flat silicon oxide film is stable in a tensile form).

FIG. 8A, Heavily wrinkled (compressive intrinsic stress) PECVD silicon oxide membrane with no anneal; FIG. 8B, Slightly less wrinkled (compressive intrinsic stress) PECVD silicon oxide membrane with N$_2$ anneal; and FIG. 8C, Flat (tensile intrinsic stress) PECVD silicon oxide membrane with H$_2$/N$_2$ anneal. FIG. 8D, FIG. 8E and FIG. 8F, are histograms of the pixel values in images FIG. 8A, FIG. 8B, and FIG. 8C, respectively. Histograms quantitatively show a narrow Gaussian distribution of pixel values for the flat membrane due to its obvious uniformity. Wrinkles cause the pixel value distribution to broaden significantly and become non-Gaussian and asymmetric. FIG. 8G, FIG. 8H and FIG. 8I, are lateral profiles of the pixel values from left to right across the center of the membranes in images FIG. 8A, FIG. 8B, and FIG. 8C, respectively. The profile is quantitatively flat and uniform for the flat membrane (features on left and right define the membrane support near the edge of the membrane). Wrinkles cause significant noise and variability around the average pixel value in the profiles for the wrinkled membranes. The amount of variability is roughly proportional to the amount of deflection in the actual membrane cause by the wrinkles.

FIG. 9A, SiN (Nitride) membrane with a Geltrex™ non-gel coating at 44 hours (at 40×). FIG. 9B, PECVD silicon oxide membrane with a Geltrex™ non-gel coating at 42 hours (at 40×).

DETAILED DESCRIPTION OF THE DISCLOSURE

Figure 1:
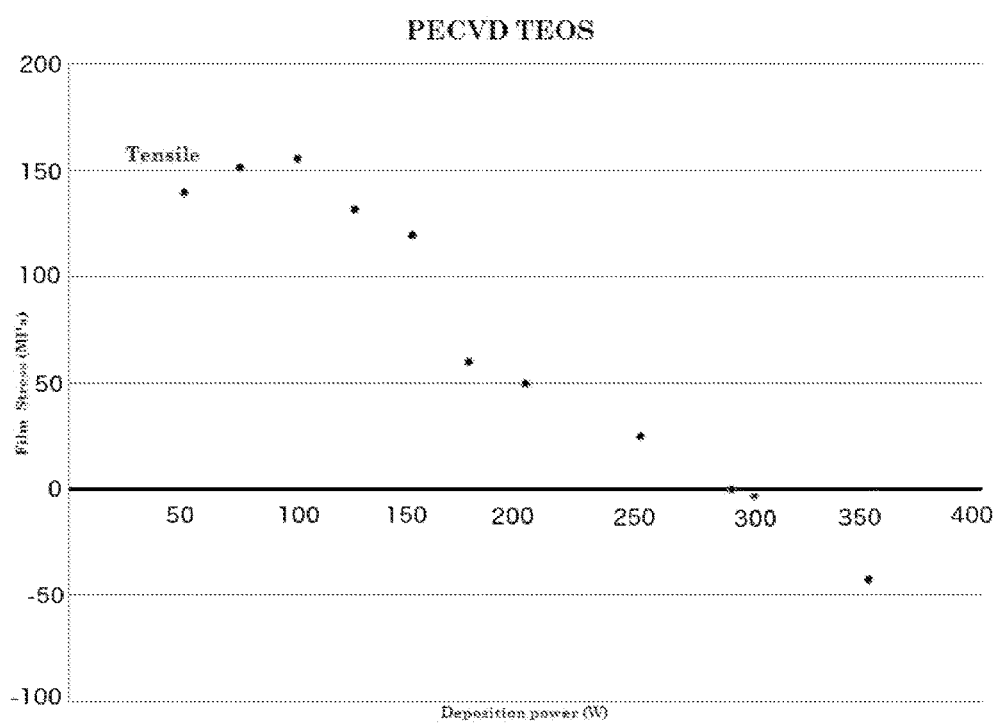
FIG. 1. A plot of nonannealed PECVD silicon oxide stress as calculated from wafer-bow measurements (using standard profilometry) vs. deposition power.
Figure 2:
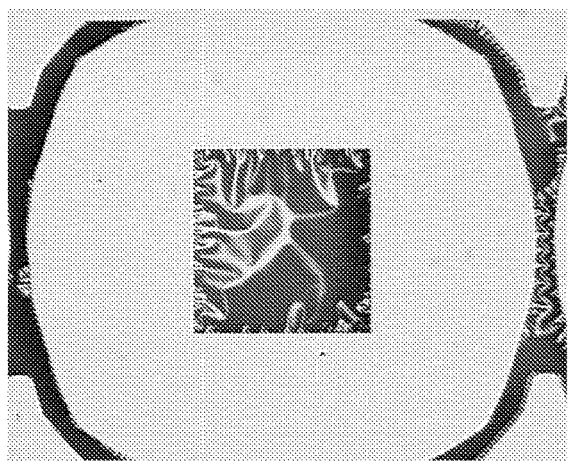
FIG. 2. An optical image of a 100 nm-thick PECVD silicon oxide membrane (non-annealed).
Figure 3:
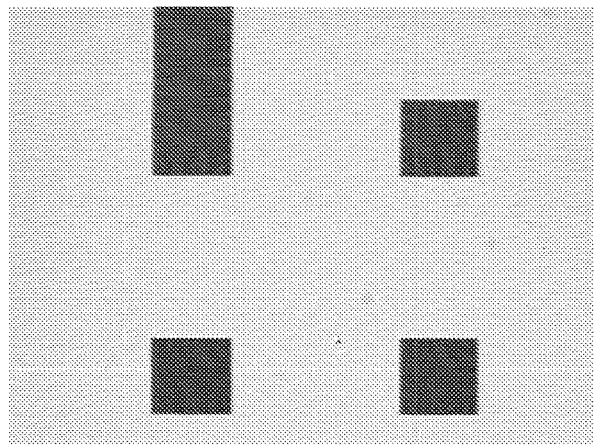
FIG. 3. Optical images of 40 nm-thick PECVD silicon oxide membranes (non-annealed).

The present disclosure provides free-standing silicon oxide membranes under tensile stress. Also provided are methods of making and using the membranes.

It was surprisingly found that stable free-standing films under tensile stress could be realized by depositing PECVD (plasma enhanced chemical vapor deposition) silicon oxide films under low RF (radio frequency) power conditions to provide films under tensile stress and subsequently subjecting the films to a thermal anneal process under forming gas ($H_2/N_2$).

In an aspect, the disclosure provides free-standing silicon oxide membranes (e.g., free-standing PECVD silicon oxide membranes) under tensile stress. By free-standing membrane it is meant that at least a portion of two surfaces of the film are exposed and not in contact with another solid material (e.g., a substrate). For example, the free-standing membrane is a layer (or film) on a substrate where at least a portion (or a plurality of portions) of the membrane is not in contact with the substrate (or any other material/layer). The as-deposited films are under tensile stress and over time become less tensile and can eventually revert to a compressively stressed state, which is the typical stress of a silicon oxide film deposited by standard methods (thermal, evaporation, sputtering, CVD, etc.) This is typical only for PECVD oxide films deposited with low power. Oxide films deposited by standard methods are typically compressive. The oxide films deposited with PECVD and, optionally, annealed in nitrogen as described above, can be referred to as "metastable" films because the film can be held in a tensile state for a finite period of time (e.g., at least 7 to 21 days), however the film stress can (depending on the annealing conditions) tend to revert to a compressive state in ambient conditions. Also, this increase in compressive stress is accelerated when the silicon oxide film is subjected to a base etchant, such as ethylenediamine pyrocatechol (EDP), which is used to suspend the membranes by removing the silicon wafer substrate under the designated membrane locations. Typical exposure to EDP ranges from 1 minute to over an hour at ~110 C.

The free-standing silicon oxide membranes are under a tensile stress of 5 MPa to 350 MPa, including all integer MPa values and ranges therebetween. In various embodiments, the membrane is under at least a tensile stress of 5 MPa to 350 MPa for at least 1 to at least 30 days, including at least all integer numbers of days therebetween. In an embodiment, the membranes are under at least a tensile stress of 5 MPa to 350 MPa indefinitely. In various embodiments, the membrane is under a tensile stress of at least 5 MPa for at least 1 to at least 30 days, including at least all integer numbers of days therebetween. In an embodiment, the membrane is under a tensile stress of at least 5 MPa indefinitely. As used herein the term tensile stress refers to intrinsic tensile stress of the membrane.

The free-standing silicon oxide membranes, e.g., as deposited or after subsequent process steps such as the thermal annealing step, have a range of composition. For example, the membrane can be a stoichiometric silicon oxide, i.e., $SiO_2$. As another example, the membrane can be a sub-stoichiometric silicon oxide, i.e., $SiO_{2-x}$, where x is from 0 to 1.9. The composition of the membranes can be altered by the various processing steps used to form the membrane. The membranes can have various surface chemistry, i.e., surface functional groups. The surface chemistry of the membranes can be altered by the various processing steps used to form the membranes or additional process steps known in the art. For example, the membranes can be functionalized with organic silane chemistries or coated with thin layers of dielectrics, metals, insulators, or semiconductors using atomic layer deposition, sputtering, CVD, PECVD, evaporation, etc.

The membranes can be microporous. For example, the membranes have a plurality of pores having a diameter of 100 nm to 1 mm, including all values to the nm and ranges therebetween. The pores can be formed by methods known in the art. For example, the pores can be formed using standard photolithography and transferred into the membrane using wet or dry etch methods.

The free-standing silicon oxide membranes can have a variety of sizes (e.g., thickness, length, width, and area). The membranes can have a thickness of 20 nm to 5000 nm, including all values to the nm and ranges therebetween. The membranes can have an area of 0.05 $mm^2$ to 400 $mm^2$. The membranes can have a length of 0.01 mm to 20 mm and a width of 0.01 mm to 20 mm.

The films are substantially flat. By substantially flat it is meant that the films do not have observable wrinkles. As used herein, wrinkles are deviations in the surface of the film as compared to a planar film. For example, a wrinkle has a deviation of at least 5 nm. Wrinkles can be observed by optical imaging methods like Nomarski or other interferometer methods known in the art. Smoother (flat) surfaces provide higher optical contrast and do not produce imaging artifacts created by the wrinkles.

The free-standing silicon flat oxide membranes exhibit a desirable optical intensity uniformity. For example, the flat membranes exhibit an optical intensity uniformity of 4% to 8% or at least 4%.

The free-standing silicon oxide membranes can be a layer on a substrate. The substrate can comprise multiple layers other than the free-standing silicon oxide membranes. Examples of suitable substrates include silicon, glass, GaN, silicon on insulator (SOI), plastic, silicone, fluoropolymer, metal, and ceramic substrates. Examples of other layers include organic materials, silicon oxide, SiN, $Al_2O_3$, and metals.

In an aspect, the disclosure provides methods of making free-standing silicon oxide membranes. The methods are based on deposition of a PECVD silicon oxide film under low RF power and subsequently subjecting the film to a thermal annealing process in a forming gas ($H_2/N_2$) atmosphere.

The PECVD films are deposited under a low RF power. The PECVD films can be deposited by PECVD methods known in the art. For example, PECVD precursors such as TEOS and $SiH_4/N_2O$ can be used. The films can be a layer on a substrate. For example, the films are deposited under a power of 50 Watts to 150 Watts, including all integer Watt values and ranges therebetween. In an embodiment, the films are deposited under a RF power of 80 Watts to 120 Watts.

Subsequent to deposition, the PECVD silicon oxide films are subjected to a thermal annealing process. Without intending to be bound by any particular theory, it is considered that the annealing process results in one or more of the following: densification of the film, lowering of porosity, sealing the outer pores to prevent infiltration of water or surface reactive species, and/or passivation/stabilization of inner nanoporous surfaces. The tensile stress of a thermally annealed PECVD silicon oxide film is increased for annealing temperatures ranging from 600° C. to less than 800° C. For annealing temperatures of 800° C. or greater, the PECVD silicon oxide becomes more compressive following thermal anneal (FIG. 5). Also, the tensile stress of a thermally annealed film can be increased relative to a film that is not so annealed. Annealing increases the stability of the film, i.e., the films are under tensile stress for a longer period of time relative to the film that is not so annealed.

The films are thermally annealed in an atmosphere comprising nitrogen, in an atmosphere comprising hydrogen and an inert gas (e.g., hydrogen and nitrogen a forming gas atmosphere), or in a hydrogen gas atmosphere. For example, the atmosphere is forming gas comprising hydrogen gas and nitrogen gas. For example, the atmosphere comprises 1% to 10% by volume hydrogen gas and 90% to 99% by volume nitrogen gas, another inert gas (e.g., argon), or a mixture thereof. In an embodiment, the atmosphere consists of 5% by volume hydrogen gas and 95% by volume nitrogen gas. In an embodiment, the atmosphere consists of nitrogen or consists of hydrogen gas and nitrogen gas. For example, the atmosphere comprises 1% to 100% by volume hydrogen gas, including all integer percent values and ranges therebetween. In an embodiment, the atmosphere comprises 0.001% to 100% by volume hydrogen gas, including all integer percent values and ranges therebetween.

The thermal annealing process is carried out at a temperature of 550° C. to 800° C., including all integer ° C. values and ranges there between. In an embodiment, the process is carried out at a temperature of 600° C. to 700° C. In another embodiment, the process is carried out at a temperature of 600° C. to 650° C. The thermal annealing is carried out for at least 0.1 hour to at least 8 hours, including all 0.1 at least hour(s) values and ranges therebetween. In an embodiment, the thermal annealing is carried out for at least 1 hour to at least 8 hours, including at least all integer numbers of at least hours therebetween. In an embodiment, the thermal annealing is carried out for 0.01 hour to 24 hours, including all integer numbers of hours and ranges therebetween. In an embodiment, the thermal annealing is carried out for 1 hour to 24 hours, including all integer numbers of hours and ranges therebetween.

The thermally annealed films are also more resistant to base etchants. In an embodiment, the PECVD silicon oxide films are deposited on a substrate configured such that at least a portion of the film is exposed after contacting the substrate with a base etchant (e.g., EDP and KOH) providing a free-standing silicon oxide film of the present disclosure. The substrate is as described herein.

The following is an example of a method of forming PECVD silicon oxide membranes. A method of preparing the membrane comprises depositing a layer of PECVD silicon oxide to one side of a substrate and, optionally, thermally annealing the silicon oxide layer, where the opposite side of the substrate is masked. These steps can be performed in either order. After masking and applying the PECVD silicon oxide, the substrate is etched, beginning from the masked opposite side of the substrate and continuing until a passage is formed through the substrate, thereby exposing the film on both sides thereof to form the free-standing silicon oxide membrane.

Figure 10:
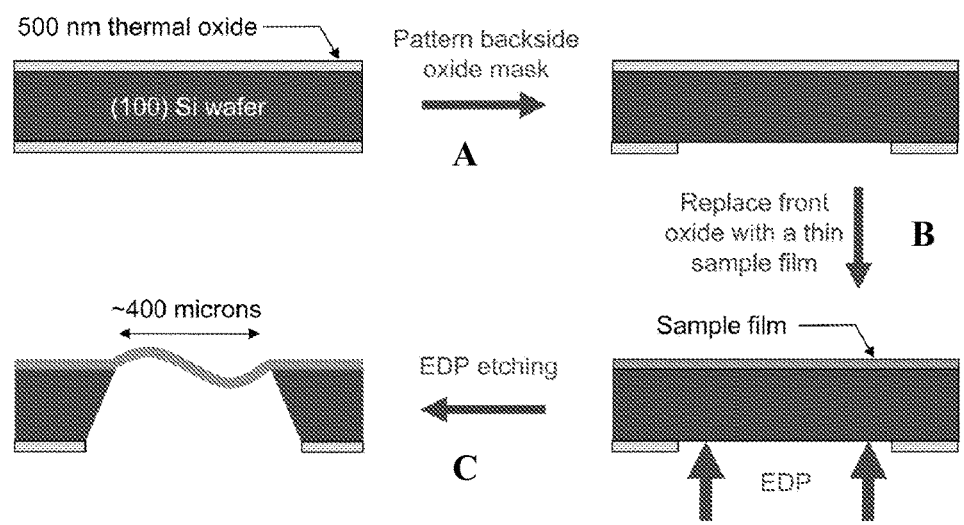
FIG. 10. A schematic illustration of an embodiment of making a membrane of the present disclosure. References to silicon, silicon dioxide, and EDP etchant are by way of example only.

These steps are described in greater detail in association with the schematic illustration of FIG. 10. Although FIG. 10 refers to silicon, silicon dioxide, and EDP etchant, it should be appreciated that such references are by way of example only.

The substrate to be used to support the PECVD silicon oxide membranes is a substrate that can be easily masked and etched so that a membrane can be formed. silicon is an example of such a substrate. Using standard 4, 6, 8, or 12 inch silicon wafers as the support, upwards of about 1500, 500 µm×500 µm, of the membranes can be formed on the surface of the membrane depending on the desired linear area to be occupied by the membrane. Using silicon as the example, silicon contains a naturally occurring native oxide layer. To simplify the procedures used in preparing and forming the films of the present disclosure, this native oxide layer can be removed entirely from one side of the substrate and partially removed (i.e., during the masking procedure) from the opposite side of the substrate, in both instances using a buffered oxide etchant ("BOE") such as, but not limited to, "buffer HF improved" etchant (Transene Company Inc., Danvers, Mass.). This is illustrated in Steps A and B, respectively, of FIG. 10. However, this masking can also be achieved with a thermally grown silicon oxide layer or any other common masking material like SiN. This film can be patterned using standard photolithography and reactive ion etching, other dry etching or wet etching techniques.

Figure 11:
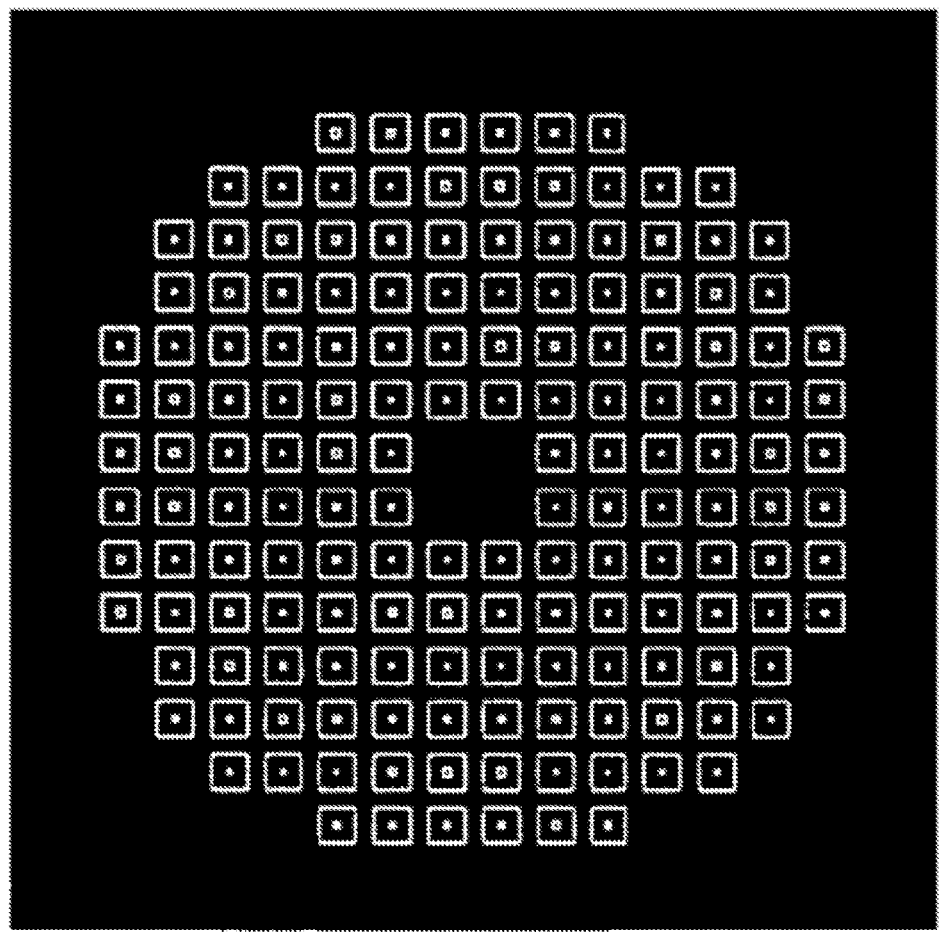
FIG. 11. An illustration of the backside masking of elements so as to facilitate formation of an etched passage through the substrate (i.e., to expose the membrane) as well as a trench in the substrate to allow for removal of an individual membrane.

The masking step can be performed by forming an array of elements that will dictate the manner in which the unprotected substrate will be etched. According to an embodiment, illustrated in FIG. 11, each element is composed of a square hole surrounded by a square outline. This allowed the formation of membrane structures, and also cut a trench around each membrane so that samples could be individually removed from the wafer. Other configurations can, of course, be utilized without departing from the scope of the disclosure. The backside silicon oxide can be patterned with standard photolithography, followed by, for example, a 10 minute soak in 4:1 BOE or a 3-5 minute soak in 10:1 BOE to transfer the pattern into the oxide layer. The photoresist can be removed with acetone.

To the side of the substrate that lacks the oxide layer, the PECVD silicon oxide is applied and, optionally, the silicon oxide is thermally annealed. This is illustrated in Step B of FIG. 10.

As noted above, the etching process is carried out beginning from the backside (i.e., masked side) of the substrate. This process is illustrated in Step C of FIG. 10.

The steps of the methods described herein are sufficient to produce the PECVD silicon oxide membranes of the present disclosure. Thus, in an embodiment, the method consists essentially of a combination of the steps of the method disclosed herein. In another embodiment, the method consists of such steps.

In an aspect, the disclosure provides uses of the free-standing silicon oxide membranes. For example, the membranes can be used as substrates in imaging methods, such as cell imaging methods and can be useful as substrates for electron microscopy.

It is desirable to use the membranes of the present disclosure in imaging methods because the membranes have low refractive index (nearly invisible when submerged in water), high transparency (little or no wavelengths are blocked, even in the UV range), high optical contrast, general biological inertness, biocompatibility (e.g., cells adhere and grow), and ease of surface functionalization/modification (known silane chemistries react with silicon oxide surface groups by design).

In an embodiment, a method of imaging an object comprises: preparing a sample for imaging comprising one or more objects disposed on at least a portion of a surface of a free-standing PECVD silicon oxide of the present disclosure; and obtaining an image of at least one of the objects or at least a portion of one of the objects.

In an embodiment, a method of imaging an object comprises: preparing a sample for imaging comprising one or more objects disposed on at least a portion of a surface of a free-standing PECVD silicon oxide membrane of the present disclosure; and obtaining an image of at least one of the objects or at least a portion of one of the objects.

Examples of objects that can be imaged include cells (such as single or multiple prokaryotic or eukaryotic cells), sub-cellular constituents, viruses, particles, powders, thin-films, and the like.

The image can be obtained by, for example, optical microscopy, fluorescence microscopy, confocal microscopy, two-photon microscopy, electron microscopy, and the like.

The steps of the methods described herein are sufficient to image the one or more of the object(s)s or at least a portion of the one or more object(s) of the present disclosure. Thus, in an embodiment, the method consists essentially of a combination of the steps of the method disclosed herein. In another embodiment, the method consists of such steps.

The following specific examples are provided to illustrate the instant disclosure, but are not intended to be limiting in any manner.

Example 1

This example describes the deposition of PECVD silicon oxide films and thermal processing of the films.

PECVD silicon oxide films were deposited under the following conditions:
Susceptor Temperature: 390° C.
$O_2$ Flow: 285 sccm
TEOS Flow: 400 sccm
Pressure: 9 Torr
RF Power: 100 W-150 W
Deposition Rate: ~8 nm/sec PECVD silicon oxide was deposited in a tensile form by adjusting the deposition power. Maximum tensile stress was achieved around 100 W. Decreasing deposition power did not affect TEOS deposition rate. PECVD silicon oxide deposited as tensile was considered 'metastable'. The as deposited PECVD silicon oxide has limited stability in the bases used to realize membranes. As a result, nonannealed PECVD silicon oxide and PECVD silicon oxide thermally annealed in nitrogen that had been exposed to base etchants (EDP and
KOH) became compressive (wrinkled) (See, e.g., FIGS. 2, 3, FIG. 8A, FIG. 8B.)

A thermal anneal (in forming gas ($H_2/N_2$)) resulted increased resistivity of the PECVD silicon oxide in bases, such as EDP or KOH. The thermal anneal increased the stability of the tensile form of the PECVD silicon oxide (i.e., the flat silicon oxide membranes). (See, e.g., FIG. 8C.)

Figure 4:
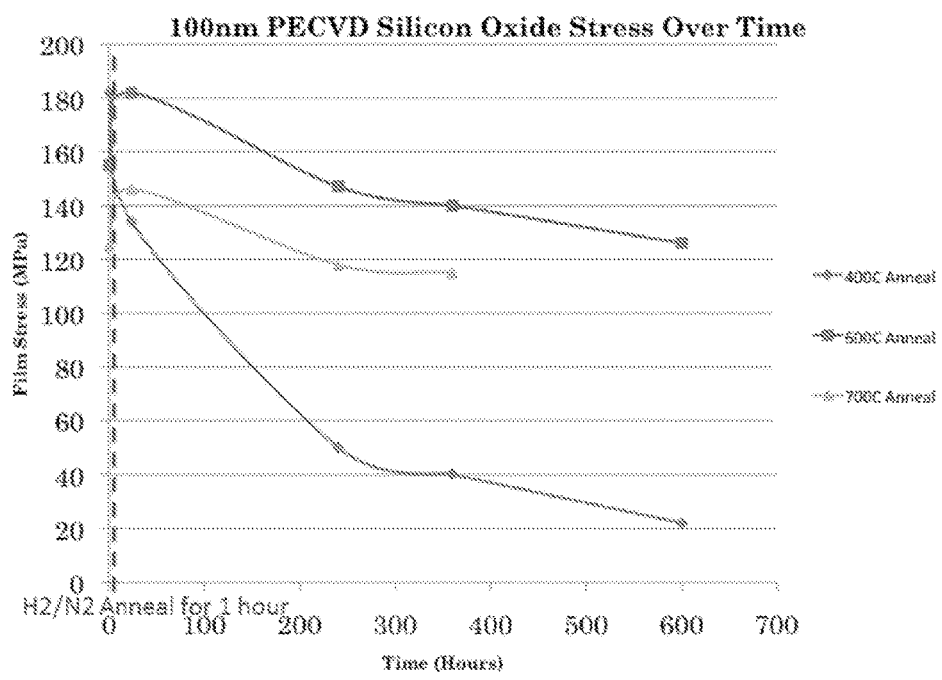
FIG. 4. A plot of PECVD silicon oxide film stress vs. time (following a 1 hour anneal in H$_2$/N$_2$).
Figure 6C:
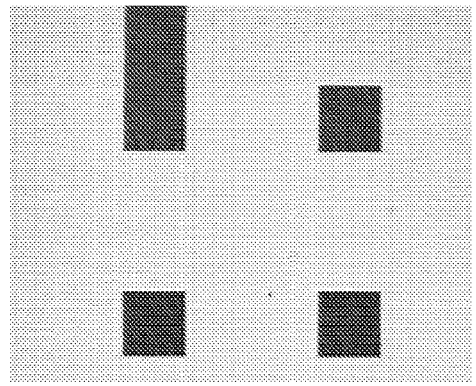
Figure 6D:
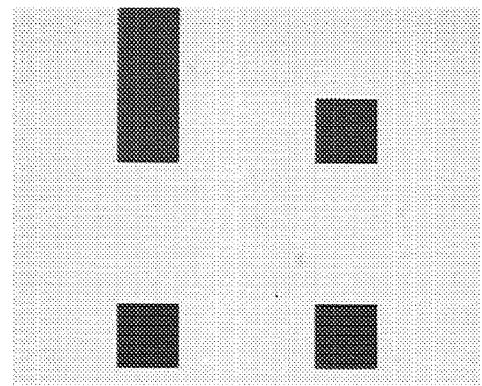

For membranes subjected to annealing immediately following deposition (1 hour), long term drift of the stress was observed. (See, e.g., FIG. 4.) A 600° C. anneal resulted in PECVD silicon oxide with increased tensile stress. (See, e.g., FIG. 5.)

Flat freestanding PECVD silicon oxide membranes resulted from low-power deposition (100 W) and $H_2/N_2$ gas anneal (600° C.) (See, e.g., FIG. 6A-FIG. 6D.)

Figure 7A:
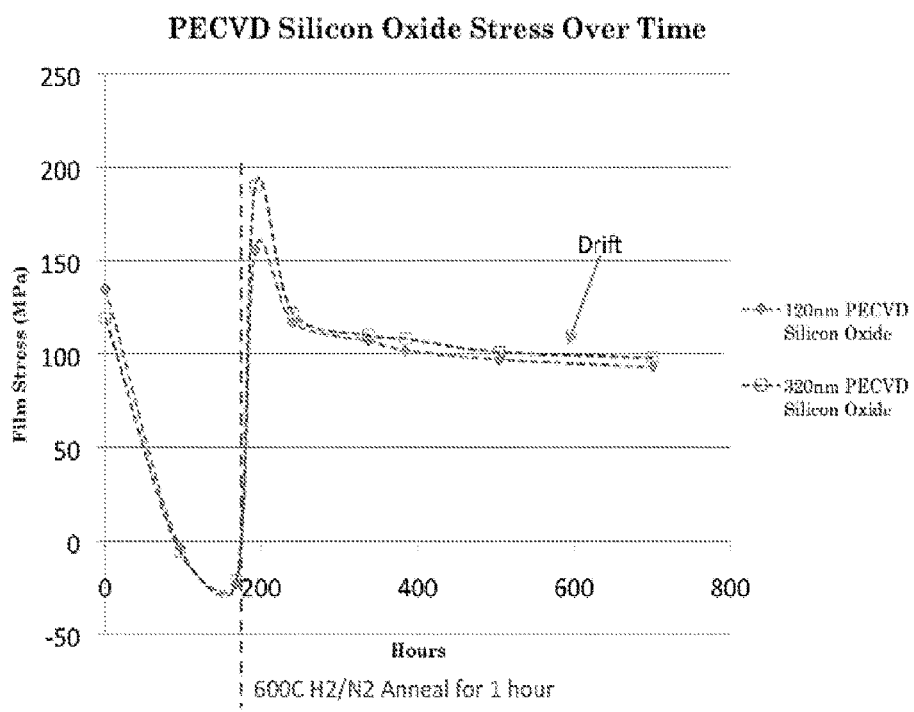
FIG. 7A-FIG. 7B. Plots of stress vs. time for metastable PECVD silicon oxide (FIG. 7A—1 hour anneal and FIG. 7B—8 hour anneal). PECVD silicon oxide deposited as tensile will become compressive in ~100 hours if left unannealed.
Figure 7B:
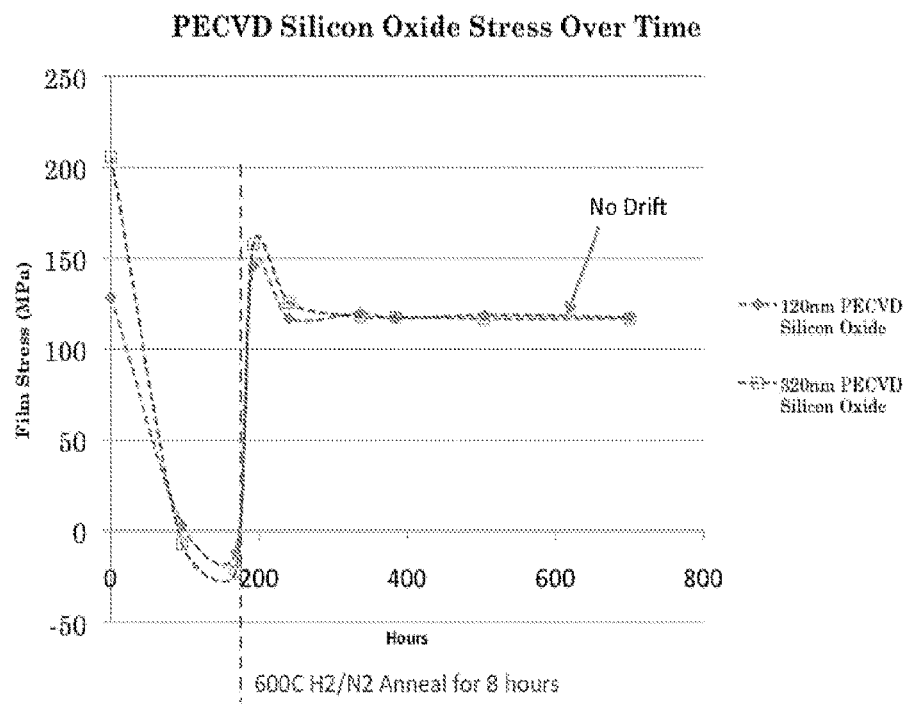
Figures 8A, 8B, 8C:
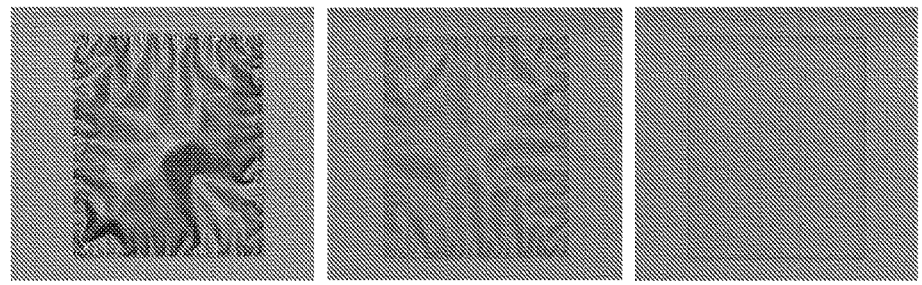
FIG. 8A-FIG. 8I. Example of silicon oxide membrane "flatness" as measured by the optical variability in the reflectance image.
Figure 8D:
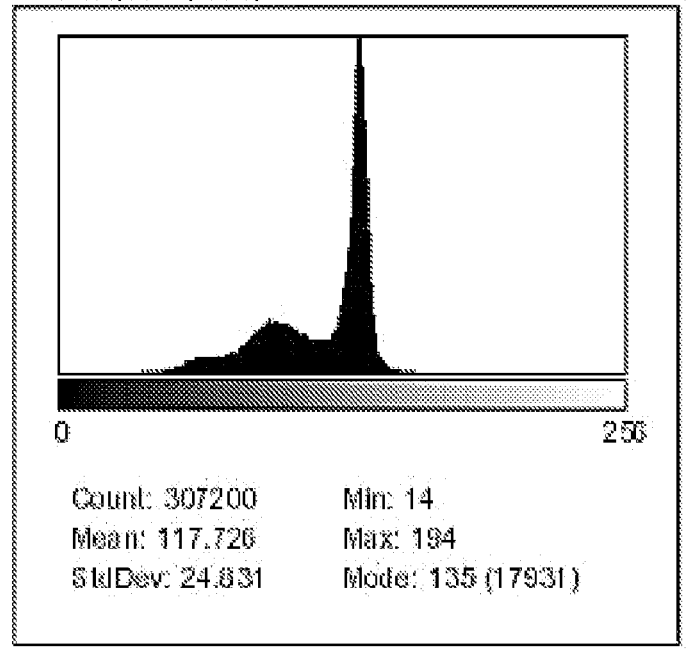
Figure 8E:
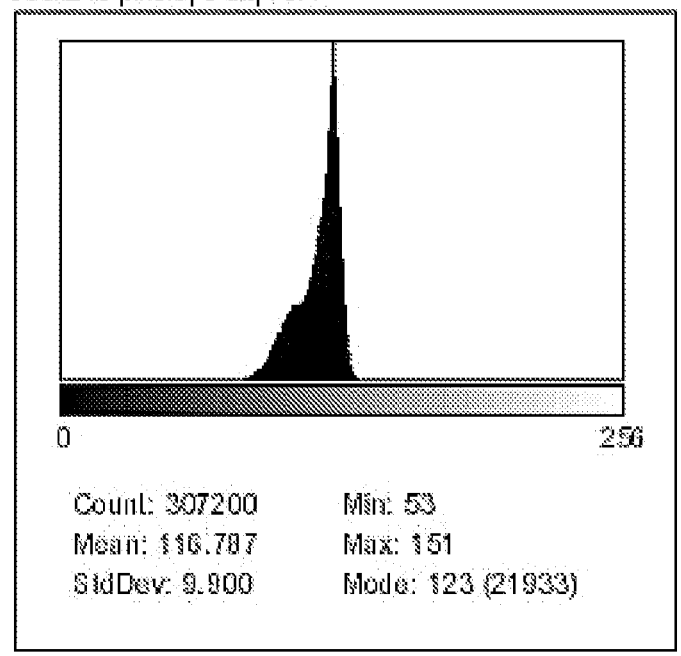
Figure 8F:
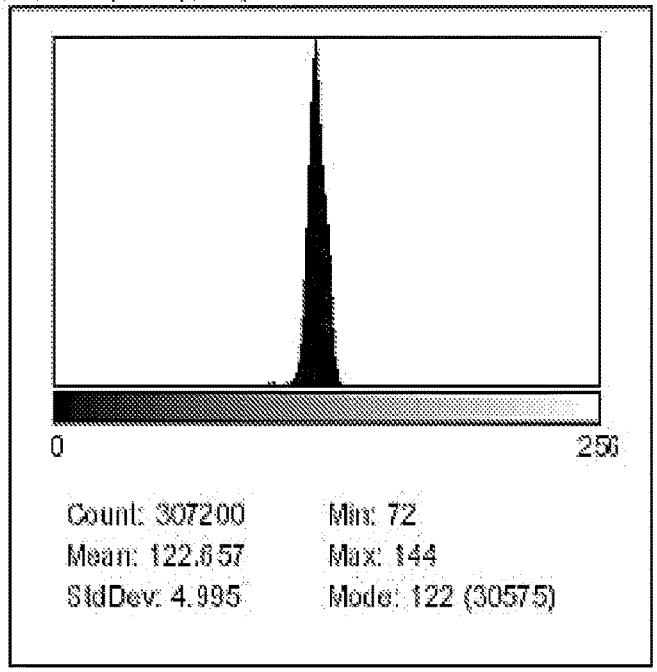
Figure 8G:
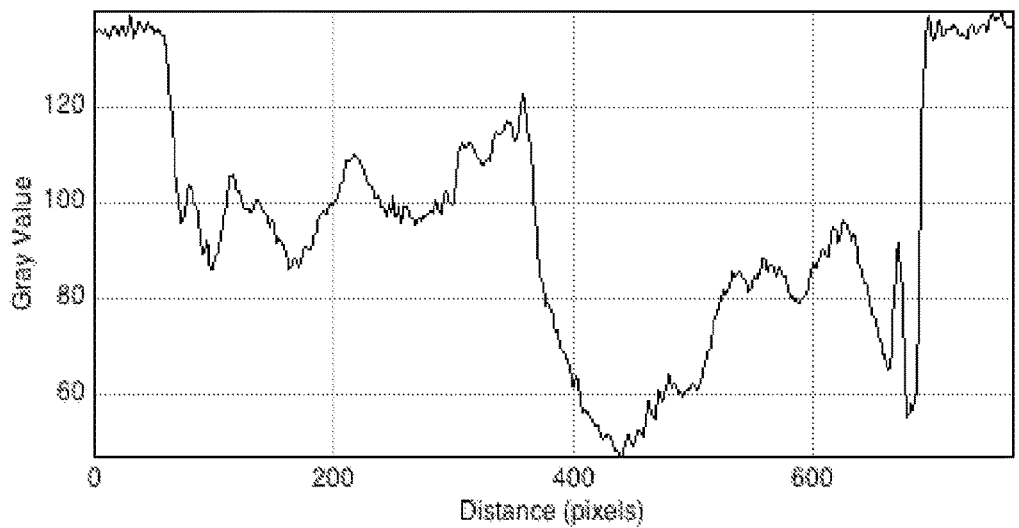
Figure 8H:
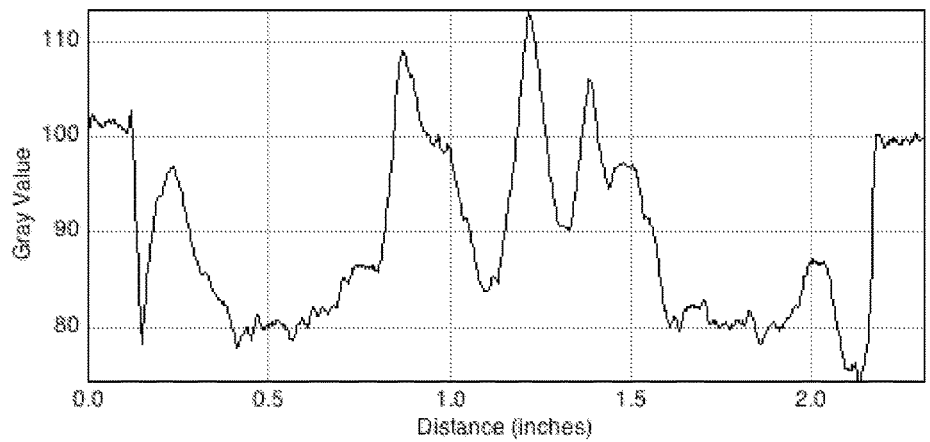
Figure 8I:
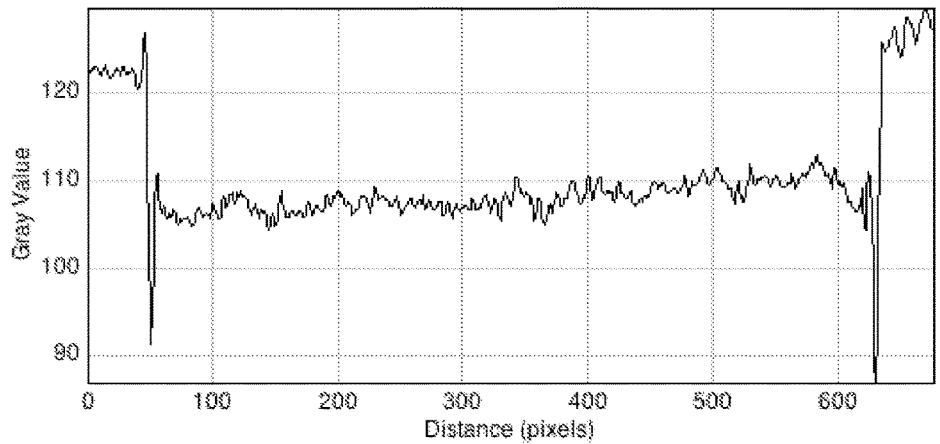

Without an anneal, PECVD silicon oxide becomes compressive in ~4 days (at standard atmosphere). Following a $H_2/N_2$ anneal for 1 hour, PECVD silicon oxide became and remained tensile, but did exhibit drift in tensile stress. (See, e.g., FIG. 7A-FIG. 7B.)

PECVD silicon oxide was made to remain tensile for a period of time as a freestanding film (membrane) by depositing the silicon oxide with low RF power PECVD and performing a forming gas ($H_2/N_2$) anneal at 600° C. Less "drift", or change in stress, is observed in the 48 hours following the 8 hour anneal, compared to the 1 hour anneal. Thickness of PECVD silicon oxide does not significantly affect the resulting stress (thicknesses of 50 nm to 400 nm were tested).

Example 2

This example describes optical imaging using free-standing silicon oxide membranes of the present disclosure.

Figure 9A:
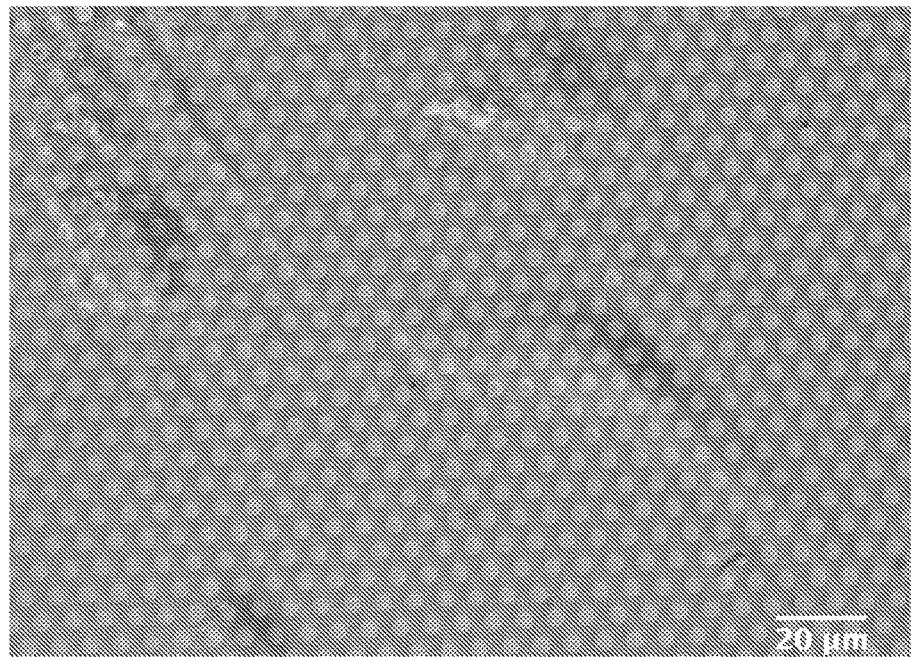
FIG. 9A-FIG. 9B. Example of improved cell imaging using a free-standing silicon oxide membrane of the instant disclosure.
Figure 9B:
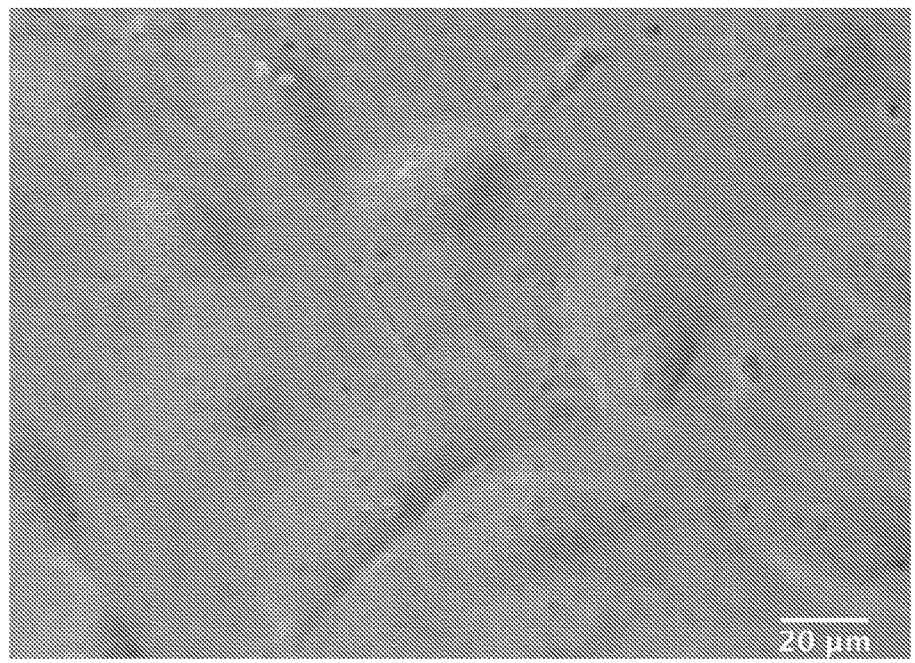

Low background noise and higher-density cell growth was observed using microporous PECVD silicon oxide when compared to the microporous silicon nitride (SiN). (See, e.g., FIG. 9A and FIG. 9B.)

Cellular imaging was improved using the tensile microporous PECVD silicon oxide when compared to industry-standard microporous nitride.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A free-standing silicon oxide film that is under at least 5 MPa of tensile stress for at least 7 days.

2. The silicon oxide film of claim 1, wherein the silicon oxide film is substantially flat.

3. The silicon oxide film of claim 1, wherein the silicon oxide film is microporous.

4. The silicon oxide film of claim 1, wherein the film has a thickness of 5 nm to 5000 nm.

5. The silicon oxide film of claim 1, wherein the film has an area of 0.0625 $mm^2$ to 400 $mm^2$.

6. A method of obtaining an image comprising:
a) providing a sample comprising one or more objects to be imaged disposed on a free-standing silicon oxide membrane of claim 1; and
b) obtaining an image of at least one object or at least a portion of one object.

7. The method of claim 6, wherein the one or more objects are cells, sub-cellular constituents, viruses, particles, powders, thin-films, or a combination thereof.

8. The method of claim 6, wherein the image is obtained by optical microscopy, fluorescence microscopy, confocal microscopy, two-photon microscopy, or electron microscopy.

9. A method of forming a free-standing silicon oxide film that is under at least 5 MPa of tensile stress for at least 7 days comprising:
a) depositing a silicon oxide film using plasma-enhanced chemical vapor deposition (PECVD) on a substrate configured to release at least a portion of the silicon oxide film as a free-standing film, wherein said PECVD is configured to deposit said silicon oxide film under tensile stress;
b) annealing the silicon oxide film in an atmosphere comprising hydrogen and nitrogen using a thermal process; and
c) exposing at least a portion of the silicon oxide film such that a free-standing silicon oxide film is formed.

10. The method of claim 9, wherein said PECVD occurs at an RF power between 80 W and 120 W.

11. The method of claim 9, wherein said thermal process is carried out at a temperature between 550° C. and 700° C.

12. The method of claim 9, wherein said thermal process has a duration between approximately 1 hour and approximately 8 hours.

13. The method of claim 9, wherein the silicon oxide film is substantially flat after the annealing step.

* * * * *